US011623942B2

(12) United States Patent
Lihme et al.

(10) Patent No.: US 11,623,942 B2
(45) Date of Patent: Apr. 11, 2023

(54) METHOD FOR PURIFYING PROTEINS USING SILICATE

(71) Applicant: Lihme Protein Solutions APS, Farum (DK)

(72) Inventors: Allan Otto Fog Lihme, Farum (DK); Marie Bendix Hansen, Frederiksberg (DK)

(73) Assignee: Lihme Protein Solutions ApS, Farum (DK)

(*) Notice: Subject to any disclaimer, the term of this patent is extended or adjusted under 35 U.S.C. 154(b) by 742 days.

(21) Appl. No.: 16/491,970

(22) PCT Filed: Mar. 7, 2018

(86) PCT No.: PCT/EP2018/055604
§ 371 (c)(1),
(2) Date: Sep. 6, 2019

(87) PCT Pub. No.: WO2018/162557
PCT Pub. Date: Sep. 13, 2018

(65) Prior Publication Data
US 2020/0190139 A1  Jun. 18, 2020

(51) Int. Cl.
*C07K 1/32* (2006.01)
*A23J 1/00* (2006.01)
*A23J 1/08* (2006.01)

(52) U.S. Cl.
CPC .................. *C07K 1/32* (2013.01); *A23J 1/006* (2013.01); *A23J 1/008* (2013.01); *A23J 1/08* (2013.01)

(58) Field of Classification Search
CPC ... C07K 1/32; A21J 1/006; A23J 1/008; A23J 1/08
USPC ........................................................ 530/420
See application file for complete search history.

(56) References Cited

U.S. PATENT DOCUMENTS 2,588,392 A    3/1952  Julian et al.

FOREIGN PATENT DOCUMENTS

| CN | 1477197 | 2/2004 | |
| CN | 103087147 | 4/2015 | |
| WO | WO2005056808 | 6/2005 | |
| WO | WO-2008056977 A1 * | 5/2008 | .............. A23J 1/006 |
| WO | WO2016036243 | 3/2016 | |
| WO | WO2018162557 | 9/2018 | |

OTHER PUBLICATIONS

CN 1 477 197—Machine Translation (Year: 2004).*
Coradin, T. et al. Colloids and Surfaces B: Biointerfaces, 35: 53-58 (Year: 2004).*
Kong, X. et al., "Recovering proteins from potato juice by complexation with natural polyelectrolytes", Internation Journal of Food Science & Technology, vol. 50(10), pp. 2160-2167, (Oct. 2105).
Jimenez-Atienzar, M. et al., "Determination of the phospholipase activity of patatin by a continuous spectrophotometric assay", Lipids, vol. 38(6), pp. 677-682, (Jun. 2003).
Spelbrink, R. et al., "Quantitative determination of trypsin inhibitory activity in complex matrices". The Open Food Science Journal, vol. 5, pp. 42-46, (2011).
Yoruk, R. et al., "Physiochemical properties and function of plant polyphenol oxidase: a review", Journal of Food Biochemistry, vol. 27(5), p. 361-422. (2003).
Bauw, G. et al., "Patatins, Kunitz protease inhibitors and other major proteins in tuber of potato cv. Kuras", The FEBS Journal, vol. 273(15), pp. 3569-3584, (2006).
Anthon, G. et al., "Colormetric method for the determination of lipoxygenase activity", J. Agric. Food Chem., vol. 49, pp. 32-37, (2001).

* cited by examiner

*Primary Examiner* — Hamid R Badr
(74) *Attorney, Agent, or Firm* — McHale & Slavin, P.A.

(57) ABSTRACT

The present invention relates to method for purifying proteins using silicates.

17 Claims, 12 Drawing Sheets

1 2 3 4 5 6 7 8

METHOD FOR PURIFYING PROTEINS USING SILICATE

CROSS REFERENCE TO RELATED APPLICATIONS

This is a national stage filing in accordance with 35 U.S.C. § 371 of PCT/EP2018/055604, filed Mar. 7, 2018, which claims the benefit of the priority of Denmark Patent Application No. PA 2017 70160, filed Mar. 7, 2017, the contents of each are incorporated herein by reference.

FIELD OF THE INVENTION

The present invention relates to method for purifying proteins using silicates.

BACKGROUND OF THE INVENTION

The present invention relates to methods for purifying proteins using soluble silicates and proteins purified by such methods.

Techniques for industrial scale isolation of proteins from complex liquid raw materials have been a target of constant development for more than a century. Very many different methods based on various physico-chemical parameters have been described in the prior art but only few have found industrial applicability.

Purified proteins may be of value in widely different areas such as pharmaceutical, food, feed and technical applications and for each specific application there will be different target specifications for the purity and functionality of the protein. Likewise, the market value for a certain protein depends on the type of application. Thus, proteins intended for pharmaceutical applications have a much higher market value than proteins intended for food or feed applications. It is therefore crucial that any methodology, and its associated process cost, chosen for the isolation of a protein is carefully balanced against the value of the protein.

Precipitation of proteins from aqueous solutions is widely used for large scale separation. Proteins may be precipitated by adding various agents such as organic solvents, lyotropic salts (such as ammonium sulfate) or polymers of different kind. Many food proteins are isolated from plant extracts (such as aqueous extracts of soy beans and peas) by so-called isoelectric precipitation which is based on the natural tendency of some proteins to become insoluble at pH values where the protein surface exhibits a near zero net charge. Isoelectric precipitation of proteins is generally a very low-cost operation. However, the method has limitations due to a rather low selectivity, co-precipitation of other unwanted substances and a narrow window of operation. A major drawback of the isoelectric precipitation method is that it is difficult to remove the co-precipitated impurities by washing of the precipitated proteins because any change of the conditions (such as pH, temperature and ionic strength) may lead to solubilization and loss of the protein. Another major drawback of the isoelectric precipitation method is that only certain proteins will precipitate, leaving significant amounts of otherwise valuable proteins in the mother liquid and thereby lead to economic losses and environmental burdens from the associated waste water. Precipitation of proteins by the addition of chemical substances such as organic solvents, lyotropic salts and polymers is not generally applied for the industrial separation of food and feed grade proteins due to the high costs associated with the chemicals, the high costs of chemicals recycling and treatment of waste water and the need to completely remove these chemicals from the product after the precipitation process.

Precipitation of proteins from aqueous solutions may also be performed by the application of heat, such as heating to 110-130 degrees Celsius under increased pressure, or by heating combined with adjustment of pH to highly acidic pH values. Such processes are industrially applied, for example in order to precipitate potato proteins from potato fruit juice produced as a side-stream in the potato starch manufacturing industry. Such processes may be highly efficient; however, the proteins will be completely denatured by the process conditions. Typically, such treated proteins will be largely insoluble and any biological activity and functional characteristics will be lost.

Membrane filtration is another widely and industrially used method for the isolation and concentration of proteins from complex mixtures. The fundamental separation principle is based on the passing of the liquid through semipermeable membranes allowing only the passage of molecules smaller than the size of the porous structure of the membrane. Thus, membrane filtration separates molecules largely on the basis of their size and the availability of membranes with different pore sizes enables the separation of molecules and particles of varying size ranges. However, in order to achieve an efficient separation, the molecules to be separated must have very different sizes (such as at least 10 times different size). Molecules being closer in size will only be partially separated which may be detrimental to the product yield and thereby the economy of the separation process.

Solid phase adsorption (adsorption chromatography) is based on the reversible interaction of molecules in a solution with the surface structures of an insoluble adsorbent material. Silica gels, in the form of silicon dioxide beads or coarse granules, constitute a specific type of solid phase adsorbents that may be produced with varying pore size and available surface area. Agarose beads and synthetic polymer beads constitute other groups of solid phase adsorbents with different characteristics for different protein separation tasks. The surface of the insoluble adsorbent material may be chemically derivatized to facilitate interaction with molecules of widely different nature and can be designed to achieve highly selective separation of even closely related molecules. Thus, solid phase adsorption is widely applied in the manufacture of proteins for pharmaceutical applications.

The use of a solid phase adsorbent for isolation of proteins typically comprises the following steps:

Equillibration of the solid phase adsorbent, which involves washing of the adsorbent with buffers that conditions the adsorbent surface to the pH and ionic strength suitable for binding of the target molecule Conditioning of the liquid raw material, which typically involves adjustment of pH and ionic strength suitable for binding of the target molecule to the sloid phase adsorbent Contacting the solid phase adsorbent with the liquid raw material for a time span sufficient to ensure diffusion of the target molecule into the porous structures of the adsorbent and allow a binding equilibrium to take place Washing of the solid phase adsorbent with buffers to remove unwanted impurities Elution of the target molecule by incubation with buffers changing the conditions such that the bound molecules are released and diffuse out of the adsorbent for collection.

Cleaning of the adsorbent to ensure complete removal of all bound substances prior to reusing the adsorbent. This is typically performed with highly caustic or highly acidic chemical agents comprising detergents and other aggressive cleaning agents. This step is important to avoid carry-over of substances from cycle to cycle and to avoid, or delay, a gradual inactivation of the adsorbent surface by irreversible fouling of very hard binding substances.

Re-equilibration of the adsorbent to make it ready for a repeated cycle of target molecule binding.

Due to the high selectivity of solid phase adsorption this methodology has attracted much attention for separation tasks requiring high product purity. However, the cost of the adsorbents, the time-consuming cycling between binding and release of target molecules and the high water and chemicals consumption for washing, cleaning and regeneration of the adsorbents all adds to the high cost of using this separation technology. Therefore, solid phase separation is only rarely used for the isolation of food and feed grade proteins.

Compounds such as proteins and metabolites comprised in plants are valuable and useful in many different applications such as nutrition, medical treatments, cosmetics and acceptable process aids for industrial manufacture of the same. Particularly, such proteins and metabolites in significant crop plants, such as potatoes, are interesting and become even more valuable and useful in isolated form. Potatoes, for example, contain useful patatins and protein inhibitors which are desirable to use in isolated and purer forms.

Kong et al. (Recovering proteins from potato juice by complexation with natural polyelectrolytes; International Journal of Food Science and Technology 2015, 50, 2160-2167) relates to characterization of potato proteins and their protein-polyelectrolyte complexes.

Waglay & Karboune (Potato Proteins: Functional Food Ingredients; Chapter 4; Advances in Potato Chemistry and Technology, 08 2016) disclose potato proteins prepared by various methods including thermal coagulation, acidic precipitation, precipitation with salt, ethanol, ammonium sulfate or CMC, anion-exchange chromatography or size exclusion separation.

However, many plants, including potatoes, also contain compounds that are undesirable or even poisonous in some applications. Particularly, potatoes (belonging to the night shade family) contain several compounds which are undesired for some applications, while useful in other applications. Patatins and protease inhibitors are useful in nutrition and nutraceutical application, while glycoalkaloids (toxic), Lipoxygenase (rancidify fats/oils), polyphenol oxidase (oxidizes and tans food stuff) or phenolic compounds are not desired in nutrition and nutraceutical application.

Additionally, the use of adsorption chromatography for the industrial scale production of proteins have proven difficult to establish commercially due to the high cost of chromatographic adsorbents, the low productivity associated with running adsorption columns and the high water and chemicals consumption associated with washing, eluting regenerating and cleaning chromatographic columns.

On the other hand, isolated glycoalkaloids are useful in certain cosmetic or pharmaceutical applications.

Accordingly, there is a need for methods for separating and/or isolating functional compounds to be used in industrial application.

SUMMARY

In a first aspect, the present invention relates to a method for isolating one or more proteins from an aqueous protein solution comprising said one or more proteins and impurities, the method comprising;
 a. providing an aqueous solution containing the one or more proteins and the impurities
 b. adding a water-soluble silicate to the solution of step a) such that the total concentration of silicon in the form of free or complexed silicates in the solution is in the range of 1-1000 mM,
 c. if necessary, adjusting the pH of the resulting solution to a pH in the range of pH 1 to pH 11,
 d. allowing the silicate to form an insoluble precipitate of a silicate-protein complex,
 e. separating the silicate-protein complex from the solution as a wet precipitate; such as a wet cake or an aqueous suspension of the precipitate,
 f. optionally washing the silicate-protein complex to further remove said impurities from the silicate-protein complex,
 g. optionally separating the one or more proteins from the silicate,
thereby obtaining the isolated protein product.

In a second aspect, the invention relates to a method for purifying a protein in an aqueous solution comprising impurities, the method comprising;
 a. providing an aqueous solution containing the protein and the impurities at pH 2-12,
 b. adding a soluble silicate to the solution of step a) such that the concentration of silicon (in the form of silicate) in the solution is in the range of 1-500 mM,
 c. adjusting the pH of the resulting solution to pH 5-7,
 d. allowing the silicate to form an insoluble silicate-protein complex,
 e. separating the silicate-protein complex from the solution, and
 f. separating the protein from the silicate,
thereby obtaining the purified protein.

Other aspects of the technology are evident from the appended claims and the following description.

DETAILED DISCLOSURE OF THE INVENTION

Figure 1:
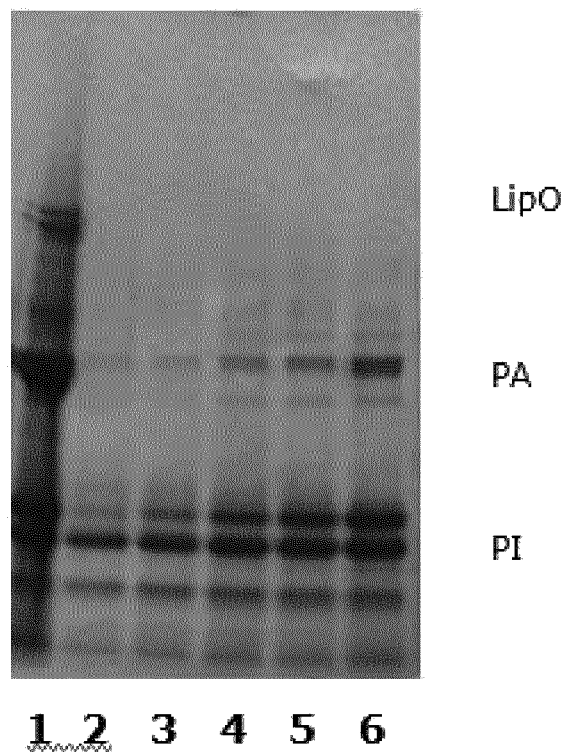
FIG. 1 is a Coomassie Blue stained SDS-PAGE gel illustrating the separation of proteins of test solutions 1-6 described in Example 1.

The term "anionic compound" means a compound that comprise a negatively charged moiety at a pH in the range of pH 3 to pH 13.

The term "patatin", also denoted herein as "PA", means storage glycoproteins found in potatoes (Solanum tuberosum). Patatin represents a group of immunologically identical glycoprotein isoforms with molecular mass in the range of 40-43 kDa. Patatin also have phospolipase activity capable of cleaving fatty acids from membrane lipids. For purposes of the invention PA may be determined by different known assays, including SDS-PAGE combined with scanning densitometry as described herein (e.g. using a GS-900™ Calibrated Densitometer from BIO-RAD Laboratories, USA) including all protein bands in the molecular weight region between 35 kD and 60 kD the PA category, ELISA testing using patatin specific antibodies, as well as enzymatic assays specific for the phospholipase activity (see e.g. Lipids, 2003, 38(6):677-82. "Determination of the phospholipase activity of patatin by a continuous spectrophotometric assay." Jiménez-Atiénzar M et al.

The term "protease inhibitor", also denoted herein as "PI", means proteins, which possess molecular weights ranging from about 3 kD to about 35 kD, e.g. found in potatoes (Solanum tuberosum) and other plants such as soy and lupin, animals and microorganisms capable of inhibiting the activity of e.g. serine proteases, cysteine proteases, aspartate proteases, and metalloproteases. For purposes of the invention PI, in e.g. potato derived samples, may be determined by different known assays, including SDS-PAGE combined with scanning densitometry as described herein (e.g. using a GS-900™ Calibrated Densitometer from BIO-RAD Laboratories, USA) including all protein bands in the molecular weight region between 3 kD and 35 kD in the PI category, and more broadly by enzyme inhibition assays as generally described in the art (see e.g. The Open Food Science Journal, 2011, 5:42-46. "Quantitative Determination of Trypsin Inhibitory Activity in Complex Matrices". Robin E. J. Spelbrink et al.).

The term "polyphenol oxidase", also denoted herein as "PPO", means proteins found in nearly all plant tissues including potatoes (Solanum tuberosum), and can also be found in bacteria, animals, and fungi. Polyphenol oxidase (tyrosinase) (TY) is a bifunctional, copper-containing oxidase having both catecholase and cresolase activity. PPO causes the rapid polymerization of o-quinones to produce black, brown or red pigments (polyphenols) which cause fruit browning. The amino acid tyrosine contains a single phenolic ring that may be oxidised by the action of PPOs to form o-quinone. Hence, PPOs may also be referred to as tyrosinases. The catalytic action of PPO has a negative impact on the quality of several fruit and vegetable crops and results in alteration of color, flavor, texture, and nutritional value. It is a limiting factor in the handling and technological processing of crops as peeled, sliced, bruised or diseased tissues rapidly undergo browning. For purposes of the invention PPO may be determined by different known assays as reviewed in: Journal of Food Biochemistry 2003, 27(5):361-422. "Physicochemical properties and function of plant polyphenol oxidase: A review". Ruhiye Yoruk et al.

The term "lipoxygenase", also denoted herein as "LipO", means proteins found in found in plants, animals and fungi capable of catalyzing the dioxygenation of polyunsaturated fatty acids. Lipoxygenases have food-related applications in bread making and aroma production but they also have negative implications for the color, off-flavour and antioxidant status of plant-based foods. In potatoes (Solanum tuberosum) lipoxygenase has a molecular weight of approx. 97 kD and can be detected by SDS-PAGE (see e.g. FEBS Journal, 2006, 273, 3569-3584 "Patatins, Kunitz protease inhibitors and other major proteins in tuber of potato cv. Kuras" Guy Bauw et al.). For purposes of the invention LipO may be determined by different known assays, including SDS-PAGE combined with scanning densitometry as described herein (e.g. using a GS-900™ Calibrated Densitometer from BIO-RAD Laboratories, USA) as wells as enzyme activity assays as described in e.g. J. Agric. Food Chem., 2001, 49, 32-37. "Colorimetric Method for the Determination of Lipoxygenase Activity". Gordon E. Anthon et al.

The term "dry weight" means the weight or mass of a substance remaining after removal of water by heating to constant weight at 110 degrees Celcius. The dry weight per ml sample is thus the weight or mass of a substance remaining after removal of water by heating to constant weight at 110 degrees Celcius per ml sample applied to drying.

The term "isolating" or "separating" means any human intervention which change the relative amount of the compound compared to another selected constituent in a given matrix to a higher relative amount of the compound relative to the other constituent. In an embodiment, the compound may be isolated into a pure or substantially pure form. In this context, a substantially pure compound means that the compound preparation contains less than 10%, such as less than 8%, such as less than 6%, such as less than 5%, such as less than 4%, such as less than 3%, such as less than 2%, such as less than 1%, such as less than 0.5% by weight of other selected constituents. In an embodiment, an isolated compound is at least 50% pure, such as at least 60% pure, such as at least 80% pure, such as at least 90% pure, such as at least 91% pure, such as at least 92% pure, such as at least 93% pure, such as at least 94% pure, such as at least 95% pure, such as at least 96% pure, such as at least 97% pure, such as at least 98% pure, such as at least 99% pure, such as at least 99.5% pure, such as 100% pure by dry weight.

The term "membrane separation process" refers to a process using a semi-permeable membrane, allowing only compounds having a size lower that a certain value to pass, to separate molecules of a higher size in a liquid or gas continuous phase composition from molecules of a lower size. In this context, liquid or gas continuous phase compositions are to be understood in the broadest sense, including both single phase compositions such as solutions or gases, and dual phase compositions such as slurries, suspensions or dispersions wherein a solid is distributed in a liquid or gas phase.

The term "retentate" means compounds which are not allowed to pass a selected membrane in a which have a membrane separation process.

The term "permeate" or "filtrate" means compounds which canhas passed a selected membrane in a which have a membrane separation process.

The term "precipitation" refers to the phenomenon that a dissolved compound exceeding its solubility in the solvent undergoes a phase transition from a dissolved liquid state to a solid state. Precipitation is often caused by a chemical reaction and/or a change in the solution conditions. The solidified compound is referred to as the "precipitate".

The term "diafiltration" means a technique that uses ultrafiltration membranes to completely remove, replace, or lower the concentration of salts or solvents from solutions containing proteins, peptides, nucleic acids, and other biomolecules. The process selectively utilizes permeable (porous) membrane filters to separate the components of solutions and suspensions based on their molecular size. An ultrafiltration membrane retains molecules that are larger than the pores of the membrane while smaller molecules such as salts, solvents and water, which are 100% permeable, freely pass through the membrane. In a diafiltration process the retentate is added water or a buffer composition while the membrane filtration process continuously removes water, salts and low molecular weight compounds to the permeate side of the membrane.

The term "adsorption" means a process in which molecules from a gas, liquid or dissolved solid adhere to a surface of a solid phase adsorbent. Likewise, and adsorbent (also named a solid phase adsorbent) is an insoluble material on which adsorption can occur.

The term "potato" means the tubers of plant genus *Solanum*, particularly the species *S. tuberosum*.

The term "protein concentration" means the amount of protein per liter of a sample calculated as the total weight or mass of amino acids per liter as determined according to EUROPEAN PHARMACOPOEIA 5.0 section 2.2.56. AMINO ACID ANALYSIS or by determination of total nitrogen in a sample by the method of Kjeldahl using the conversion factor N×6.25. All samples are dialyzed against demineralized water in dialysis tubing cellulose membrane (Sigma-Aldrich, USA, cat. No.: D9652) to remove any free amino acids and low molecular weight peptides prior to the amino acid determination.

The term "soluble" means solubility in water at a concentration of at least 1 g/L at 25 degrees Celsius.

The term "comprise" and "include" as used throughout the specification and the accompanying items/claims as well as variations such as "comprises", "comprising", "includes" and "including" are to be interpreted inclusively. These words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The key findings of the present technology are that adjustment of the pH of a solution comprising protein, silicate and impurities allows for a selective and reversible precipitation and separation of a silicate-protein complex. The protein can therefore be separated from the impurities using selective silicate complex formation and the reversible nature of the precipitation enables the subsequent separation of the protein from the silicate This separation is very useful for industrial purposes, e.g. the purification of vegetable proteins or mammalian proteins from samples or batches that comprises impurities. Examples of such samples includes potato juice and mammalian plasma.

A first method for isolating one or more proteins from an aqueous protein solution comprising said one or more proteins and impurities is thus provided, the method comprising;

a. providing an aqueous solution containing the one or more proteins and the impurities
b. adding a water-soluble silicate to the solution of step a) such that the total concentration of silicon in the form of free or complexed silicates in the solution is in the range of 1-1000 mM,
c. if necessary, adjusting the pH of the resulting solution to a pH in the range of pH 1 to pH 11,
d. allowing the silicate to form an insoluble precipitate of a silicate-protein complex,
e. separating the silicate-protein complex from the solution as a wet precipitate;
such as a wet cake or an aqueous suspension of the precipitate,
f. optionally washing the silicate-protein complex to further remove said impurities from the silicate-protein complex,
g. optionally separating the one or more proteins from the silicate, thereby obtaining the isolated protein product. If step g. is included, the "isolated protein product" is said one or more proteins"; if step g. is excluded, the "isolated protein product" is a silicate-protein complex.

In one aspect, said washing step f) is mandatory. In another aspect, said separating step g) is mandatory. Said first method may further comprising a step of clarification to remove insoluble and/or colloid particles prior to step b).

In this first method, separation of the one or more proteins from the silicate may be done by adjusting the pH of the wet precipitate to a pH in the range of pH 7 to pH 12, such as a pH in the range of pH 7-pH 10, such as a pH in the range of pH 7-pH 9, such as a pH in the range of pH 8-pH 11, such as a pH in the range of pH 8-pH 10, such as a pH in the range of pH 8 to pH 9, such as a pH in the range of pH 8.5 to pH 11, such as a pH in the range of pH 8.5 to pH 9.9, such that the one or more proteins are released into solution from the precipitate while at least 50% of, such as at least 60%, such as at least 70%, such as at least 80% such as at least 85% such as at least 90%, such as at least 95% of the silicate in the protein-silicate complex remains in the form of an insoluble precipitate.

In said first method, separation of the one or more proteins from the silicate may be done by adjusting pH to below pH 5.0 such as a pH in the range of 0.1 to 4.9, such a pH in the range of pH 0.5 to pH 4.5, such as a pH in the range of 0.9 to pH 4.2, such as a pH in the range of 1.5 to pH 3.8, such as a pH in the range of pH 1.9 to pH 3.2, such as a pH in the range of 2.2 to pH 3.0 such that the one or more proteins are released into solution from the precipitate while at least 50% of, such as at least 60%, such as at least 70%, such as at least 80% such as at least 85% such as at least 90%, such as at least 95% of the silicate in the protein-silicate complex remains in the form of an insoluble precipitate.

In said first method, separation of the one or more proteins from the silicate may be done by first adjusting the pH of the wet precipitate to a pH in the range of pH 9 to pH 13, such as pH 9.5 to pH 12.5, such as pH 9.5 to pH 12.0, such as pH 9.5 to pH 11.5 such as pH 10.0 to pH 11.9 to solubilize the silicate-protein complex followed by allowing the silicate to be separated from the protein by a method selected from the group consisting of membrane filtration such as ultrafiltration using a membrane allowing the selective passage of silicate ions, selective silicate precipitation with metal-ions, selective precipitation of the protein with organic solvents, polymers or lyotropic salts, and adsorption chromatography such as ion exchange.

In another aspect, said step c) of pH adjustment is mandatory. In said first method the pH of the solution in step c. may be adjusted to a pH in the range 4-10, such as e.g. 5-7. In this first method, said one or more proteins may be a vegetable protein, a mammalian protein, a protein originating from fish and other aquatic animals, a protein originating from algae, a protein originating from fungi or a protein originating from microorganisms. Most suitably, the one or more proteins are potato proteins.

The first method may be used to separate two proteins or types of proteins (i.e. one or more first proteins form one or more second proteins) from each other when in an aqueous protein solution. In a particular aspect, therefore, said one or more proteins are one or more first proteins, and said impurities comprise one or more second proteins, such that the method provides the separated one or more first proteins and said one or more second proteins in two different fractions.

A second method according to the present invention provides a method for purifying a protein in an aqueous solution comprising impurities, the method comprising; providing an aqueous solution containing the protein and the impurities at pH 2-12, adding a soluble silicate to the solution such that the concentration of silicon (in the form of silicate) in the solution is in the range of 1-500 mM, adjusting the pH of the resulting solution to pH 5-7, allowing the silicate to form an insoluble silicate-protein complex, separating the silicate-protein complex from the solution, and separating the protein from the silicate, thereby obtaining the purified protein.

In an aspect of this second embodiment, the method further comprises a washing step after the step of separating the silicate-protein complex from the solution.

Separation of the protein from the silicate in this second method may be done by; raising the pH to more than 7, or raising pH to a pH of more than 10 to solubilize the silicate-protein complex allowing the silicate to be separated from the protein by a method selected from the group consisting of membrane filtration, selective silicate precipitation with metal-ions, selective precipitation of the protein e.g. with organic solvents or lyotropic salts, adsorption chromatography, selective precipitation with metal-ions, chromatography, and/or ultrafiltration, or lowering pH to below pH 5.

The protein according to either method of the invention may be a vegetable protein, a mammalian protein, a protein originating from a fish, a protein originating from algae, or a protein originating form seaweed. In an embodiment of either method, the protein is from a potato.

Animal blood, and in particular, bovine, porcine, fish and avian blood is an inevitable by-product of the fish and meat industry representing up to 4% of the live animal weight or 6% to 7% of the lean meat content of the carcass. Blood contains a number of compounds, which have potential commercial value and represents a valuable source of protein. Thousands of tons of blood are collected in abattoirs each year, that is either processed into blood meal and sold as low-value animal food and fertilizer or discarded as effluent. Animal blood produced in slaughterhouses represents a problematic by-product of the meat industry due to the high volumes generated and its very high pollutant load when discarded directly into the environment. However, blood and plasma contain highly valuable proteins such as hemoglobin, albumin, immunoglobulins, transferrin, fibrinogen, plasminogen, growth factors and coagulation factors that may be of good use in food and feed products as well as in dietary supplements products and pharmaceuticals. The complex nature of blood and plasma is a challenge for the identification of suitable separation and isolation methods that are capable of providing high quality products at a suitable price level.

It is thus an object of the present invention to provide a method for isolation of blood and plasma proteins using soluble silicates to achieve selective precipitation and separation of said proteins from aqueous solutions according to the invention and as demonstrated in the examples.

There has been considerable information published on the production of microbial protein for food and feed applications. The term "microbial protein" and "single cell protein" has developed two meanings. One meaning connotes the whole cell, in which the protein is contained within the confines of the cell wall and therefore is relatively nonfunctional. The other meaning connotes a protein isolated as a separate entity from the microbe. In either case, for human nutrition or as a functional protein ingredient in food, the nucleic acid content of the protein product should be reduced to below about 9% by weight, if yeast protein is a substantial source of protein in a human diet. The nucleic acid content of yeast cells, such as *Candida utilis* and *Saccharomyces cerevisiae*, is about 12 to 15 grams of nucleic acid per 100 grams of crude protein. The protein isolated from these cells also contains 12 to 15 grams nucleic acid per 100 grams of crude protein. Thus, the nucleic acid content should be reduced several fold before a substantial amount of the protein is used for human nutrition. The nucleic acid of yeast is mainly ribonucleic acid or RNA, and in this application these terms will be used interchangeably. Several methods for extraction of proteins from yeast and other microorganisms have been disclosed in the prior art, but common to all of them is that a high content of nucleic acids and/or nucleosides are extracted with the protein which has proven difficult and expensive to separate using the classical separation methods.

It is thus an object of the present invention to provide a method for isolation of microbial proteins using soluble silicates to achieve selective precipitation and separation of said proteins from aqueous extracts according to the invention.

In a preferred embodiment the one or more proteins are microbial proteins and the impurities are nucleic acids, oligonucleotides or mononucleotides In one embodiment the isolated protein contain less than 10%, such as less than 8%, such as less than 5%, such as less than 3%, such as less than 2%, such as less than 1%, such as less than 0.5%, such as less than 0.2, such as less than 0.1% nucleotides on a dry matter basis.

Eggs and ingredients derived from eggs are important food commodities; they are used in a vast number of different food formulations. Eggs contain a number of different proteins. Many of these proteins contribute to the excellent functional properties that eggs can invoke in a food system. Egg yolk contains an array of complex proteins, most of which are complexed with carbohydrate or lipid groups. Egg white (egg albumen) contains up to 40 different proteins, many of which play very important roles in the functional attributes of egg white. Some of the proteins in egg white have bioactivity, such as enzymatic and/or antimicrobial activity. Examples of such proteins are lysozyme, avidin and ovotransferrin. Other proteins, such as ovalbumin, have important functionality in food applications where e.g. foaming or gelling capabilities may be needed. In order to maximize the value of the egg white it would be beneficial to separate the two and more groups of proteins such that several added-value products with targeted characteristics can be produced as an alternative to the raw egg white.

It is thus an object of the present invention to provide a method for isolation of egg whitel proteins using soluble silicates to achieve selective precipitation and separation of said proteins from aqueous solutions according to the invention and as demonstrated in the examples. In a preferred option ovotransferrin is separated from ovalbumin in egg white or in other aqueous solutions containing ovotransferrin and ovalbumin using a method according to the invention.

In a preferred embodiment the separated ovalbumin contains less than 20%, such as less than 15%, such as less than 12%, such as less than 10%, such as less than 8%, such as less than 6%, such as less than 4%, such as less than 2%, such as less than 1% ovotransferrin on a dry matter basis.

Silicates

A silicate in the context of the present invention is an anionic compound containing silicon. Any water-soluble silicate may be employed according to the invention. Particularly preferred are the alkali metal silicates including sodium silicate which is the common name for compounds with the formula $Na_2(SiO_2)_nO$. A well-known member of this series is sodium metasilicate, $Na_2SiO_3$. Also, known as water glass or liquid glass, these materials are available in aqueous solution and in solid form.

The silicate concentration is in the range of 0.5-50 g/L in the present context may preferably be in the range of 0.5-25 g/L, 0.5-17 g/L, 1-15 g/L, 1-12 g/L, 1-10 g/L, 1-8 g/L, 1.5-20 g/L, 1.5-15 g/L, 1.5-12 g/L, 2-20 g/L, 2-15 g/L, 2-12 g/L, 2.5-20 g/L, 2.5-15 g/L, or 2.5-12 g/L. The silicate concentration may be in the range of 3-15 g/L, preferably in the range of 3-12 g/L.

In one embodiment of the invention the silicate may be an organosilicate (organosilanol) comprising a silicon covalently coupled to an organic molecule through a carbon-silicon bond wherein the organic molecule is capable of binding proteins in a reversible and selective manner as demonstrated in the examples.

In one embodiment the organosilicate is prepared by reaction of an organic molecule with a functional silane compound followed by hydrolysis to create the organosilicate.

In one embodiment the functional silane is chosen from the group of: glycidoxypropyltrimethoxysilane, glycidoxypropyltriethoxysilane, 3-glycidoxypropylmethyldiethoxysilane aminopropyltrimethoxysilane, aminopropyltriethoxysilane, N-(2-aminoethyl)-3-aminopropyl-trimethoxysilane, 3-methacryloxypropyltrimethoxysilane, 3-mercaptopropyltrimethoxysilane, 6 vinyltrimethoxysilane In preferred embodiments the organic molecule is a positively or negatively charged molecule.

In a preferred embodiment the organic molecule is a hydrophobic molecule comprising one or more aromatic rings.

In a preferred embodiment the organic molecule comprises one or more aromatic rings and one or more acidic groups.

In a preferred embodiment the organic molecule comprises a benzoic acid derivative such as 4-aminobenzoic acid, mercaptobenzoic acid and hydroxybenzoic acid.

In a preferred embodiment the ligand comprises an aromatic amine such as benzylamine.

In a preferred embodiment the organic molecule comprises an alkyl-amine such as butylamine hexylamine and octylamine.

In a preferred embodiment the organic molecule is covalently coupled to an activated silane compound, such as glycidoxypropyltrimethoxysilane In a preferred embodiment the organo-silicate is mixed with inorganic silicate in order to selectively precipitate one or more protein from a solution according to the invention.

EXAMPLES

Materials and Methods

Chemicals used in the examples herein e.g. for preparing buffers and solutions are commercial products of at least reagent grade.

waterglass, sodium metasilicate used for precipitation of proteins from Borup Kemi, Denmark, 36° BE, $SiO_2$=25-26% and $Na_2O$=7.5-8.5%.

sodium silicate solution, Sigma Aldrich, USA cat. No.: 338443, $Na_2O$=10.6%, $SiO2$=26.5% density 1.39 g/ml at 25° C.

sodium metasilicate powder (Sigma Aldrich, USA cat. No.: 307815)

calcium silicate (Sigma Aldrich, USA cat. No.: 742503)

glycidoxypropyltrimethoxysilane (Sigma Aldrich, USA, cat. no.: 440167)

4-aminobenzoic acid (Sigma Aldrich, USA, cat. no.: A9878)

4-mercaptobenzoic acid (Sigma Aldrich, USA, cat. no.: 706329)

hexylamine (Sigma Aldrich, USA, cat. no.: 219703)

benzylamine (Sigma Aldrich, USA, cat. no.: A9878).

benzylaminoethanol (Sigma Aldrich, USA, cat. no.: B22003).

Water used for conducting the experiments is all de-ionized water

Potato juice containing patatin (PA) and protease inhibitors (PI):

Potatoes of the variety Folva are obtained from a local supermarket.

The potatoes are washed and their surface are dried off before the potatoes are shredded with the peel while the liberated liquid (juice) concomitantly is separated from the main mass of insolubles using a commercial juicer (Nutrijuicer PRO) without diluting with water.

10 ml sodium sulphite (10 wt %) is added immediately to the juice and the juice is centrifuged for 10 min at 1430 G to remove any remaining insolubles such as fibers and starch.

10 kg of potatoes yields about 4.65 L of centrifuged juice (test solution 1) with a pH of 6.2 and a conductivity of 10.7 mS/cm, measured with a Seven2Go S3 conductivity meter from Mettler Toledo, Switzerland.

Egg White Solution:

Eggs are obtained from a local supermarket. The egg white is parted from the egg yolk. The egg white is diluted with 50 mM NaCl solution. 1 part of egg white is mixed with 2 parts of sodium chloride solution (test solution 2).

Porcine Plasma Fraction:

Porcine plasma stabilized with citrate was treated by ion exchange to selectively reduce the content of albumin (test solution 3).

Buffer Solutions

A 10 wt % sodium sulphite buffer solution is prepared by dissolving 10 g of sodium sulphite from Sigma Aldrich USA (cat. No.: 13471) in 100 mL water. pH was not adjusted. Measured to pH 7.7.

A 50 mM sodium chloride solution is prepared by dissolving 2.9 g of sodium chloride in 1 L of water.

SDS-PAGE Electrophoresis Reagents a) LDS sample buffer, 4× is obtained from Expedeon, USA (Cat. no.: NXB31010)
b) SDS Run buffer, 20× is obtained from Expedeon, USA (Cat. no.: NXB50500)
c) Precast 4-20% gradient gels are obtained from Expedeon, USA (Cat. no.: NXG42012K)
d) Instant Blue Coomassie staining solution is obtained from Expedeon, USA (Cat. no. ISB1L).

Assays a) SDS-PAGE Electrophoresis

The samples produced in each example are analyzed using SDS-PAGE gel electrophoresis showing the protein composition in each sample. The SDS-PAGE gel electrophoresis is performed using an electrophoresis apparatus and precast 4-20% gradient gels from Expedeon USA (Cat. no.: NXG42012K). The protein samples are mixed with LDS sample buffer and incubated for 10 minutes at 70° C. The samples are applied to a precast gel and proteins are allowed run for one hour at 200 V 90 mA in the SDS Run buffer at non-reduced running conditions. The gel is developed in the staining solution for three hours and the protein bands are evaluated by visually inspection or analyzed by scanning densitometry to quantify the amount of specific proteins in the test solutions.

b) Dry Matter Determination

A Sartorius moisture analyzer (MA37, Sartorius) is used to determine dry matter in a sample by applying 5-10 mL of a sample to the instrument. The sample is then dried at 110° C. until constant weight and the remaining dry matter is determined and calculated by the instrument.

Ultrafiltration

Samples are ultrafiltrated using a system from Spectrum Labs, USA, fitted with KrosFlo TFF system KMOi using hollow fiber ultrafiltration membranes. A membrane cut-off value of 10 kDa and a membrane area of 490 cm2 is employed (Spectrum Labs, USA cat. no.: 502-E010-10-N).

Example 1. Isolating Protein from Potato Juice Using Silicate 50 ml of potato juice produced according to materials and methods (test solution 1, true protein concentration 13 g/L) is divided into 5 samples (A through E respectively) of 10 ml juice and each mixed with 0.25 ml of a concentrated solution of sodium metasilicate, technical grade water glass (Borup Kemi, Denmark) 36-38 degrees Baumé, dry matter concentration 52 wt %. Addition of the waterglass is performed in aliquots of 0.05 ml and pH is immediately adjusted to pH 7 with 1 M hydrochloric acid in between each addition. When the full amount of water glass has been added the samples are adjusted to the following final pH values: A) 6.1, B) 5.5, C) 4.9, D) 4.5 and E) 3.9. Following incubation for 5 minutes with stirring at ambient temperature the samples are centrifuged for 5 min at 1430 G and the supernatant (test solutions 2-6) separated from the precipitate. SDS-PAGE is performed on test solutions 1 to 6 as illustrated in FIG. 1.

Lane 1: Potato juice (test solution 1)
Lane 2: Supernatant A, pH 6.1 (test solution 2)
Lane 3: Supernatant B, pH 5.5 (test solution 3)
Lane 4: Supernatant C, pH 4.9 (test solution 4)
Lane 5: Supernatant D, pH 4.5 (test solution 5)
Lane 6: Supernatant E, pH 3.9 (test solution 6)

Results:

From the SDS-PAGE of FIG. 1 it is observed that almost all the protein in the juice is precipitated with the water glass at pH 6.1 (lane 2, only a small fraction of the PI is remaining in the supernatant). It is further indicated that with decreasing pH the selectivity of the precipitation becomes pronounced such that at pH 3.9 and 4.5 (lane 5 and 6) most of the PI is in solution while almost all the patatin and LipO is precipitated.

Example 2. Isolating Protein from Potato Juice Using Silicate 50 ml of potato juice produced according to materials and methods (test solution 1, true protein concentration 13 g/L) is mixed with 0.5 ml of a concentrated solution of sodium metasilicate, technical grade water glass (Borup Kemi, Denmark) 36-38 degrees Baumé, dry matter concentration 52 wt %. Addition of the water glass is performed in aliquots of 0.25 ml and pH is immediately adjusted to pH 7 with 1 M hydrochloric acid in between each addition. When the full amount of water glass has been added the sample is adjusted to a final pH of 6.1. Following incubation for 5 minutes with stirring at ambient temperature the sample is centrifuged for 5 min at 1430 G and the supernatant (test solutions 2) is separated from the precipitate. SDS-PAGE is performed on test solutions 1 and 2 as illustrated in FIG. 2.

Lane 1: Potato juice (test solution 1)
Lane 2: Supernatant pH 6.1 (test solution 2)

Figure 2:
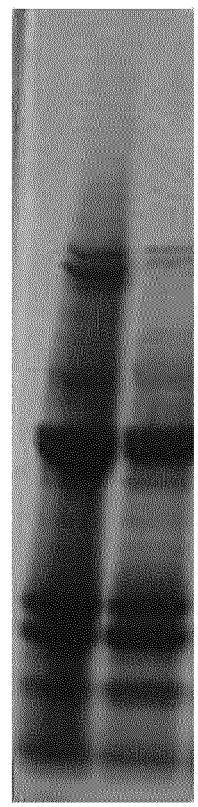
FIG. 2 is a Coomassie Blue stained SDS-PAGE gel illustrating the separation of proteins of test solutions 1 and 2 described in Example 2.

Results:

The result of the SDS-PAGE of FIG. 2 illustrates that under these conditions the precipitation is highly selective. LipO is practically absent from the supernatant while the PA and PI mainly stay in solution.

Figure 3:
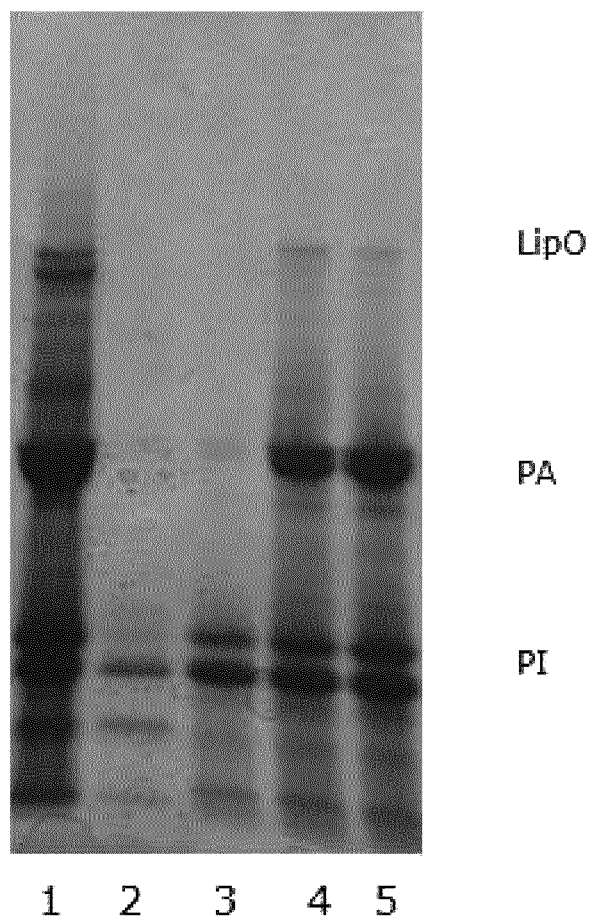
FIG. 3 is a Coomassie Blue stained SDS-PAGE gel illustrating the separation of proteins of test solutions 1-5 described in Example 3.

Example 3. Isolating Protein from Potato Juice Using Silicate 30 ml of potato juice produced according to materials and methods (test solution 1) is mixed with 1 ml of a concentrated solution of sodium metasilicate, technical grade water glass (Borup Kemi, Denmark) 36-38 degrees Baumé, dry matter concentration 52 wt %. Addition of the water glass is performed in aliquots of 0.25 ml and pH is immediately adjusted to pH 7 with 1 M hydrochloric acid in between each addition. When the full amount of water glass has been added the sample is adjusted to a final pH of 6.1. Following incubation for 5 minutes with stirring at ambient temperature the sample is divided into three 10 ml centrifuge tubes and centrifuged for 5 min at 1430 g and the supernatant from each tube is poured back into one container (test solution 2). The precipitate remaining in each centrifuge tube is washed by resuspension in 6 ml water and then centrifuged again. This procedure is repeated twice. Following the last centrifugation, the water washing supernatants are discarded while the precipitates are transferred into small beakers under addition of 6 ml water each. The beakers are labelled A-C and adjusted to varying pH values with 1 M hydrochloric acid under stirring as follows: A) pH 2.8, B) pH 1.9, C) pH 1.4. The samples are then incubated with stirring for 10 min at ambient temperature where after they are centrifuged for 5 min at 1430 g. The supernatants A), B) and C) which contain the proteins released from the precipitates are separated from the remaining precipitate to form test solution 3, 4 and 5 respectively. SDS-PAGE is performed on test solutions 1-5 and as illustrated in FIG. 3.
Lane 1: Potato juice (test solution 1)
Lane 2: Supernatant A, pH 6.1 (test solution 2)
Lane 3: Supernatant B, pH 2.8 (test solution 3)
Lane 4: Supernatant C, pH 1.9 (test solution 4)
Lane 5: Supernatant D, pH 1.4 (test solution 5)
Results:

The SDS PAGE analysis of FIG. 3 illustrates that the sodium metasilicate is able to precipitate almost all the protein present in the potato fruit juice (lane 2 which shows that only a minor fraction of the PI is left in the supernatant). Further, it can be seen, that washing of the precipitate with water and then incubating at pH 2.8 results in a highly selective release of PI proteins (lane 3) without any PA being released from the precipitate. Lowering the pH of the incubation to pH 1.9 or pH 1.4 (lane 4 and 5) results in an almost complete elution of PA and PI while the LipO remains in the remaining precipitate. The major part of the silicate is still precipitated while the proteins are in solution at pH 1.4.

For all the elutions (test solution 3-5) it is observed that the released proteins are practically colourless in contrast to test solution 1 and 2 which have a yellow/brown colour.

Figure 4:
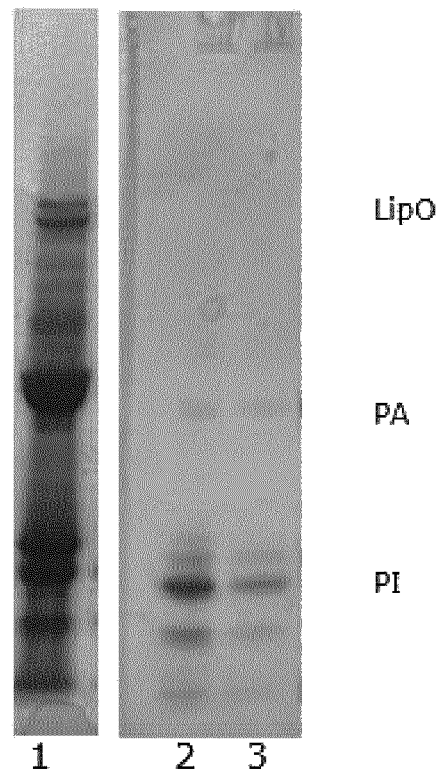
FIG. 4 is a Coomassie Blue stained SDS-PAGE gel illustrating the separation of proteins of test solutions 1, 2, and 3 described in Example 4.

Example 4. Isolating Protein from Potato Juice Using Silicate 30 ml of potato juice produced according to materials and methods (test solution 1, true protein concentration 13 g/L) is divided into 2 samples (A and B respectively) of 15 ml juice and each mixed with 0.3 ml respectively 0.6 ml of a concentrated sodium silicate solution, reagent grade water glass (Sigma Aldrich, USA cat. No.: 338443, $Na_2O$=10.6%, $SiO_2$=26.5%) density 1.39 g/ml at 25° C. Addition of the water glass is performed in aliquots of 0.15 ml and pH is immediately adjusted to pH 7 with 1 M hydrochloric acid in between each addition. When the full amount of water glass has been added the samples are adjusted to a final pH value of 6.0. Following incubation for 5 minutes with stirring at ambient temperature the samples are centrifuged for 5 min at 1430 G. The supernatants A) and B) are separated from the remaining precipitate to form test solution 2 and 3 respectively. SDS-PAGE is performed on test solutions 1, 2 and 3 as illustrated in FIG. 4.
Lane 1: Potato juice (test solution 1)
Lane 2: Supernatant A (0.3 ml water glass), pH 6.0 (test solution 2)
Lane 3: Supernatant B (0.6 ml water glass), pH 6.0 (test solution 3)
Results:

The SDS PAGE analysis of FIG. 4 illustrates that the sodium silicate solution from Sigma Aldrich is capable of precipitating almost all the protein present in the potato fruit juice at pH 6.0. The more water glass added to the juice the more protein is precipitated. Lane 2 shows that only a minor fraction of the PI is left in the supernatant A (0.3 ml water glass). Lane 3 shows even fainter bands for the PI left in the supernatant B (0.6 ml water glass).

Example 5. Isolating Protein from Potato Juice Using Sodium and Calcium Silicate (Addition of Solids to the Juice)

Figure 5:
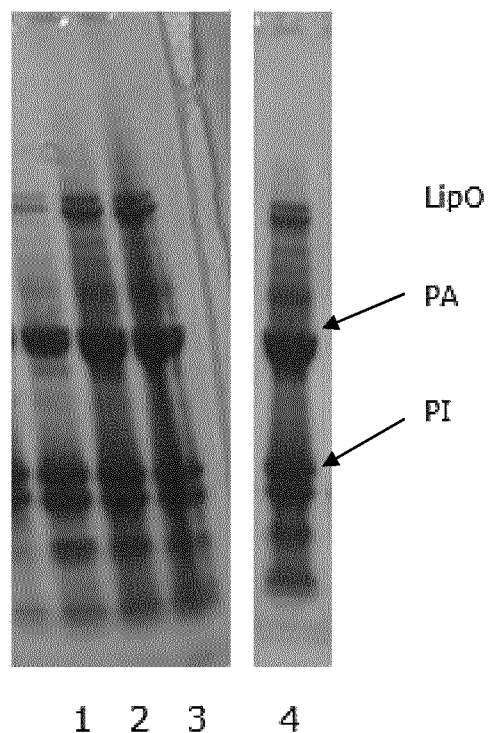
FIG. 5 is a Coomassie Blue stained SDS-PAGE gel illustrating the separation of proteins of test solutions 1, 2, 3 and 4 described in Example 5.

100 ml of potato juice produced according to materials and methods (test solution 1, true protein concentration 13 g/L) is mixed with 700 mg sodium metasilicate powder respectively 350 mg sodium metasilicate powder (Sigma Aldrich, USA cat. No.: 307815). While the mixing with the sodium metasilicate creates an increase in pH this is continuously adjusted and stabilized at pH 6.1 with 1 M hydrochloric acid over a period of 10 min. Following incubation for 15 minutes with stirring at ambient temperature the samples are centrifuged for 5 min at 1430 G. The supernatants A) and B) (respectively 700 and 350 mg sodium metasilicate) are separated from the remaining precipitate to form test solution 2 and 3 respectively. 10 ml of the same batch of potato juice (test solution 1) is mixed with 100 mg calcium silicate (Sigma Aldrich, USA cat. No.: 742503) and pH is adjusted to pH 6.0 with 1 M hydrochloric acid. Following incubation for 15 minutes with stirring at ambient temperature the sample is centrifuged for 5 min at 1430 G. The supernatant C) is separated from the remaining precipitate to form test solution 4. SDS-PAGE is performed on test solutions 1, 2, 3 and 4 as illustrated in FIG. 5.
Lane 1: Supernatant A (700 mg sodium silicate), pH 6.1 (test solution 2)
Lane 2: Supernatant B (350 mg sodium silicate), pH 6.1 (test solution 3)
Lane 3: Potato juice (test solution 1)
Lane 4: Supernatant C (calcium silicate), pH 6.0 (test solution 4)
Results:

The SDS PAGE analysis of FIG. 5 illustrates that in contrast to the addition of a sodium silicate solution (water glass, see e.g. previous examples) the addition of solid sodium silicate when adding 700 mg per 100 ml juice precipitates rather selectively the LipO while the PI stay in solution together with most of the PA (see lane 1, very weak LipO band in the supernatant A). When adding 350 mg sodium silicate per 100 ml juice the major content of potato proteins stays in solution (see lane 2). Addition of the insoluble calcium silicate does not precipitate any significant amount of proteins (see lane 4).

Example 6. Synthesis of Silicates with Organic Functional Groups

Five solutions comprising different organic functional groups and labelled A) through E) are prepared by mixing at ambient temperature as follows:
Solution A: 20 ml water is added 2 g 4-aminobenzoic acid (Sigma Aldrich, USA, cat. no.:
A9878) followed by adjustment of pH to 11.8 with 5 M sodium hydroxide.
Solution B: 20 ml water is added 2 g 4-mercaptobenzoic acid (Sigma Aldrich, USA, cat. no.:
706329) followed by adjustment of pH to 11.0 with 5 M sodium hydroxide.
Solution C: 20 ml water is added 2 g hexylamine (Sigma Aldrich, USA, cat. no.: 219703).
Solution D: 20 ml water is added 2 g benzylamine (Sigma Aldrich, USA, cat. no.:A9878).
Solution E: 20 ml water is added 2 g benzylaminoethanol (Sigma Aldrich, USA, cat. no.: B22003).

To each solution is then added 5 ml glycidoxypropyltrimethoxysilane (Sigma Aldrich, USA, cat. no.: 440167) under constant stirring and the temperature is increased to 40 degrees Celsius. The reaction is carried out for 18 hours, after which the silane has reacted covalently with the organic reactants through the glycidoxygroup and the trimethoxy groups have reacted with water to create a organo-silicate compound that may partly polymerize, the solutions are cooled to ambient temperature and each applied for dialysis against 5 L demineralized water in dialysis tubing cellulose membranes (Sigma-Aldrich, USA, cat. No.: D9652). The dialysis is continued for 48 hours at ambient temperature with 4 shifts of the water. Following removal of any surplus and unreacted reactants by dialysis acid-base titrations and elemental analysis for determination of nitrogen, sulfur and silicon confirm that the glycidoxypropyltrimethoxysilane reacts with the added organic functional groups. All solutions also form a heavy precipitate upon acidification with hydrochloric acid.

Example 7. Isolation of Potato Proteins Using Silicates Coupled with Organic Functional Groups 50 ml of potato juice produced according to materials and methods (test solution 1, protein concentration 10 g/L) is mixed with a solution of the silicate-4-mercatobenzoic acid derivative prepared according to example 6 to reach a final concentration of 10 mg silicate derivative per ml potato juice and pH is adjusted to pH 5.1 at ambient temperature. A heavy precipitate is formed. Following mixing for 5 minutes the mixture is centrifuged at 1430 g for 10 minutes. The resulting supernatant is decanted (test solution 2) and analyzed by SDS-PAGE according to materials and methods. From the SDS-PAGE analysis it is concluded that most of the PI in the sample is bound while only a smaller fraction of the PA is removed.

The example demonstrates that the coupling of silicates with organic molecules may influence the specificity of the reaction and precipitation with proteins in complex protein mixtures. Screening of organo-silicate compounds of the type prepared in example six will reveal different binding and precipitation patterns characteristic to the nature of the organic molecule coupled to the siloxane.

Figure 6:
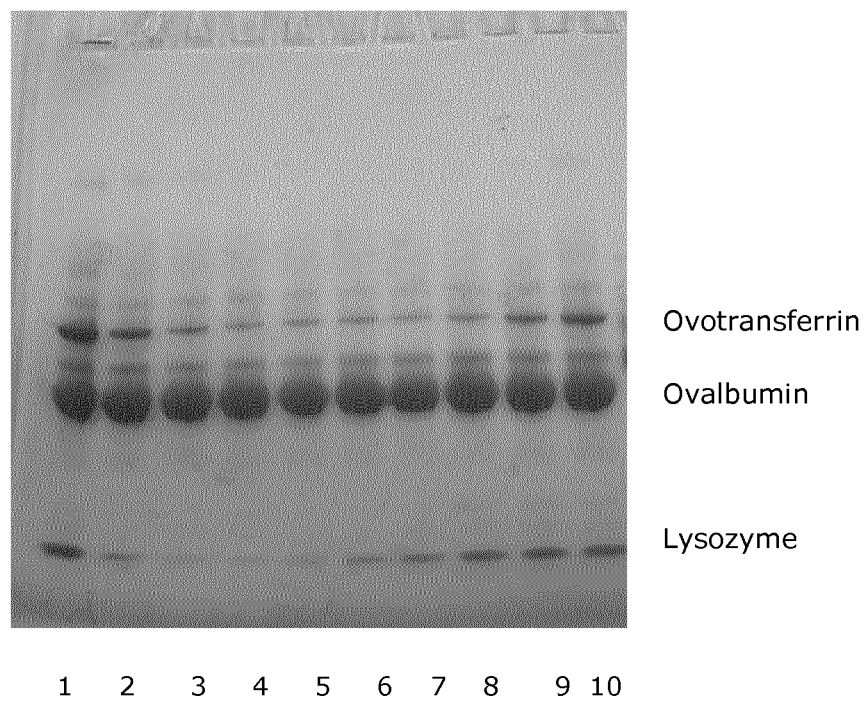
FIG. 6 is a Coomassie Blue stained SDS-PAGE gel illustrating the separation of proteins of test solutions 2-11 described in Example 8.

Example 8. Isolating Protein from Egg White Using Silicate 450 ml of egg white solution produced according to materials and methods (test solution 2) is divided into 9 samples (A through I respectively) of 50 ml white solution and each mixed with 0.833 ml of a solution of water glass (Borup Kemi, Denmark). Addition of the waterglass is performed in aliquots of 0.05 ml and pH is immediately adjusted to pH 7 with 1 M hydrochloric acid in between each addition. When the full amount of water glass has been added the samples are adjusted to the following final pH values: A) 7.6, B) 6.8, C) 6.4, D) 6.0, E) 5.5, F) 4.7, G) 4.0, H 3.4 and I) 3.0. Following incubation for 60 minutes with stirring at ambient temperature the samples are centrifuged for 5 min at 1430 G and the supernatants (test solutions 3-11) separated from the precipitate. SDS-PAGE is performed on test solutions 2 to 11 as illustrated in FIG. 6.
Lane 1: Test solution 2, egg white mixed with 50 mM NaCl
Lane 2: Test solution 3, supernatant pH 7.6
Lane 3: Test solution 4, supernatant pH 6.8
Lane 4: Test solution 5, supernatant pH 6.4
Lane 5: Test solution 6, supernatant pH 6.0
Lane 6: Test solution 7, supernatant pH 5.5
Lane 7: Test solution 8, supernatant pH 4.7
Lane 8: Test solution 9, supernatant pH 4.0
Lane 9: Test solution 10, supernatant pH 3.4
Lane 10: Test solution 11, supernatant pH 3.0
Results:
The SDS PAGE analysis of FIG. 6 illustrates that the sodium silicate solution is capable of precipitating the major part of the lysozyme in the pH-range of 6.0-6.8, the supernatants for these pH-values, see lane 3-5 only show rather faint lysozyme bands. At pH-values higher and lower this pH-range less lysozyme precipitates. The figure also illustrates that the sodium silicate solution is capable of precipitating the major part of the ovotransferrin in the pH-range of 4.0-6.8, the supernatants for these pH-values, see lane 3-8 only show rather faint ovotransferrin bands. At pH-values higher and lower than this pH-range less ovotransferrin precipitates. In the pH-range of 6-6.4 the water glass precipitates the major content of ovotransferrin and lysozyme in the egg white leaving the major part of the ovalbumin in solution.

Example 9. Isolating Egg White Proteins Using Silicate 350 ml of egg white solution produced according to materials and methods (test solution 2) is divided into 8 samples (A through H respectively) of 35 ml white solution and each mixed with 0.583 ml of a solution of water glass (Borup Kemi, Denmark). Addition of the water glass is performed in aliquots of 0.05 ml and pH is immediately adjusted to pH 7 with 1 M hydrochloric acid in between each addition. When the full amount of water glass has been added the samples are adjusted to a final pH value of 6.2. Following incubation for 60 minutes with stirring at ambient temperature the samples are centrifuged for 10 min at 1430 G and the supernatants are separated from the precipitates. The precipitates remaining in the centrifuge tubes are washed by re-suspending in 35 ml water and then centrifuged again. The proteins are released from the precipitates by adding 35 ml water, while mixing the pH is adjusted to respectively A) 4.0, B) 3.5, C) 2.5, D 2.0, E) 8.5, F) 9.5, G) 10.5 and H) 11.3. The samples are centrifuged for 10 min at 1430 G and the supernatants (test solution 3 through 10 respectively) are separated from the precipitates.

Figure 7:
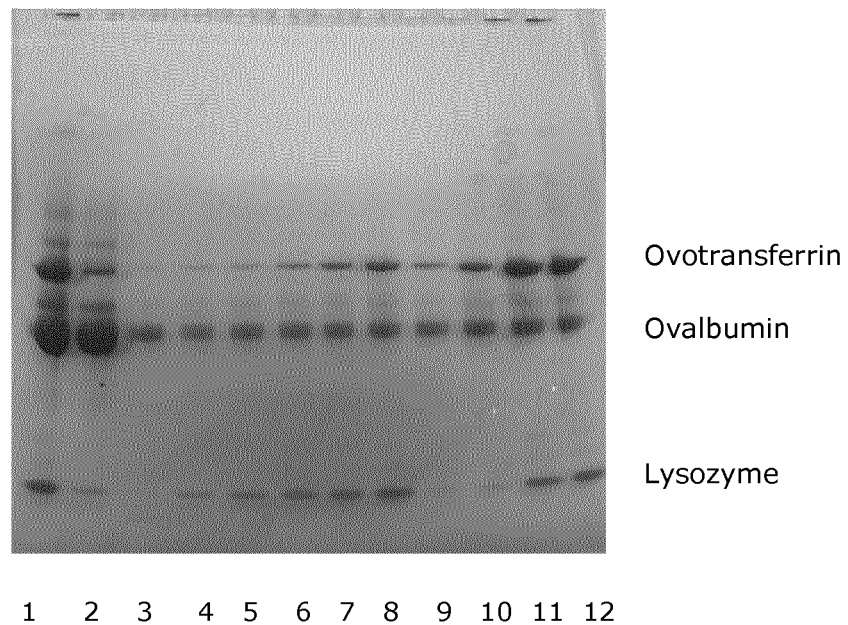
FIG. 7 is a Coomassie Blue stained SDS-PAGE gel illustrating the separation of proteins of test solutions 2-10 described in Example 9.

SDS-PAGE is performed on test solutions 2 to 10 as illustrated in FIG. 7.
Lane 1: Test solution 2, egg white mixed with 50 mM NaCl
Lane 2: Supernatant from water glass precipitation
Lane 3: Wash of precipitate with water
Lane 4: Test solution 3, proteins released at pH 4.0
Lane 5: Test solution 4, proteins released at pH 3.5
Lane 6: Test solution 5, proteins released at pH 3.0
Lane 7: Test solution 6, proteins released at pH 2.5
Lane 8: Test solution 7, proteins released at pH 2.0
Lane 9: Test solution 8, proteins released at pH 8.5
Lane 10: Test solution 9, proteins released at pH 9.5
Lane 11: Test solution 10, proteins released at pH 10.5
Lane 12: Test solution 11, proteins released at pH 11.3
Results:
The SDS PAGE analysis of FIG. 7 illustrates that the sodium silicate solution is capable of precipitating the major part of ovotransferrin and lysozyme in the egg white (lane 2, shows non-precipitated material).

After washing the precipitate, the decrease of pH releases a small amount of ovalbumin together with a fraction of the ovotransferrin and the lysozyme, the lower pH the more protein is released, see lane 3-7 while the water glass is still precipitated. At pH 8.5 and 9.5 it is mainly ovalbumin and a fraction of ovotransferrin that is released from the water glass, see lane 9 and 10. At pH 10.5 (lane 11) most of the precipitated protein is released from the water glass resulting in a highly enriched ovotransferrin/lysozyme product. At pH 10.5 most of the water glass is still precipitated. At pH-values higher than 11 the precipitate is totally dissolved and all the protein is released into solution together with the water glass.

Example 10. Isolating Egg White Proteins Using Silicate Polymers

1 L of egg white solution produced according to materials and methods (test solution 2) is mixed with 16.7 ml of a solution of water glass (Borup Kemi, Denmark). Addition of the waterglass is performed in aliquots of 2 ml and pH is immediately adjusted to pH 7 with 1 M hydrochloric acid in between each addition. When the full amount of water glass has been added the sample is adjusted to a final pH value of 6.2. Following incubation for 60 minutes with stirring at ambient temperature the sample is centrifuged for 10 min at 1430 G and the supernatant is separated from the precipitate. The precipitate remaining in the centrifuge tubes is washed by re-suspending in 1 L of water and then centrifuged again. The proteins are released from the precipitate by adding up to 1 L of water, while mixing the pH is raised to 11.1 where the precipitate is totally dissolved. The solution containing proteins and soluble silicate is then concentrated to 100 ml by ultrafiltration and then diafiltrated by addition of deionized water on a hollow fiber membrane (10 kD cut off) to concentrate the proteins in the retentate and remove the silicate in the permeate. The dry matter of the retentate is then determined and the yield is calculated.

Results:

The yield of dry matter isolated per ml of egg white is 28.7 mg. The product is a highly enriched product mainly containing ovotransferrin, lysozyme and a minor fraction of the ovalbumin separated from the water glass. Testing for the presence of silicate in the retentate showed that more than 95% of the silicate was removed by the membrane filtration.

Example 11. Isolating Proteins from Albumin-Reduced Porcine Plasma Using Silicate 90 ml of albumin-reduced porcine plasma (test solution 3) is divided into 6 samples (A through F respectively) of 15 ml plasma, different amounts of water glass (Borup Kemi, Denmark) are added. A: 750 µl, B: 500 µl, C: 375 µl, D: 300 µl, E: 250 µl and F: 188 µl. pH was adjusted in all solutions to 6.0 with 1 M HCl. Following incubation for 60 minutes with stirring at ambient temperature, the samples are centrifuged for 10 min at 1430 G and the supernatant (test solutions 4-9) separated from the precipitate. SDS-PAGE is performed on test solution 4-9 as illustrated in FIGS. 8a and 8b.

Figure 8A:
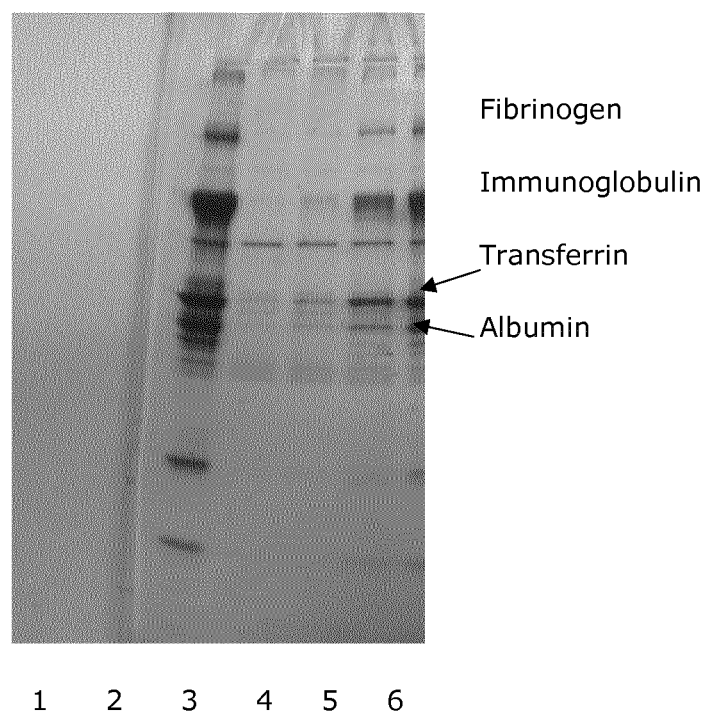
FIG. 8A is a Coomassie Blue stained SDS-PAGE gel illustrating the separation of proteins of test solutions 3, 4, 6, 7 and 8 described in Example 11.

FIG. 8a:
Lane 1: Albumin reduced porcine plasma, test solution 3
Lane 2: Supernatant, 750 µl water glass, test solution 4
Lane 3: Supernatant, 375 µl water glass, test solution 6
Lane 4: Supernatant, 300 µl water glass, test solution 7
Lane 5: Supernatant, 250 µl water glass, test solution 8
Lane 6: Supernatant, 188 µl water glass, test solution 9
FIG. 8b:
Lane 7: Albumin reduced porcine plasma, test solution 3
Lane 8: Supernatant, 500 µl water glass, test solution 5

Figure 8B:
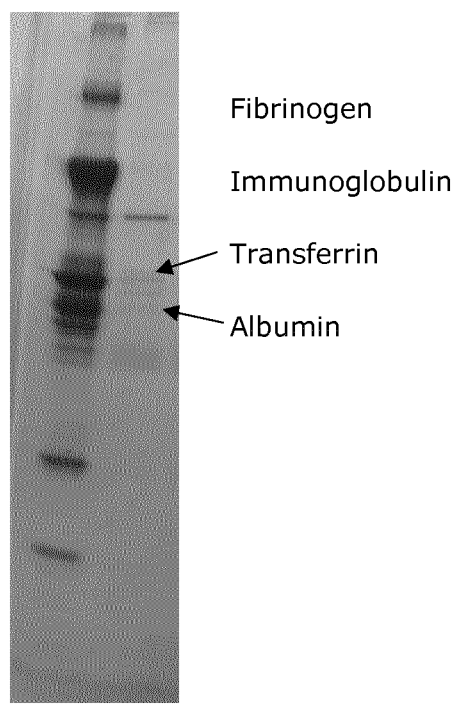
FIG. 8B is a Coomassie Blue stained SDS-PAGE gel illustrating the separation of proteins of test solutions 3 and 5 described in Example 11.

The SDS PAGE analysis of FIGS. 8a and 8b, illustrates that the sodium metasilicate solution is capable of precipitating practically all the protein present in the albumin reduced porcine plasma when adding respectively 750 µl and 500 µl water glass per 15 ml of plasma (see lane 2 and 8). Very weak bands appear for these supernatants indicating that the proteins have been precipitated.

Most of the proteins are precipitated when adding 375 µl water glass per 15 ml plasma (see lane 3). When adding less than 375 µl water glass per 15 ml plasma the concentration of non-precipitated protein in the supernatant increases (see lane 4, 5 and 6)

Example 12. Isolating Proteins from Albumin Reduced Porcine Plasma with Silicate Polymer Precipitate (#730)

120 ml of albumin reduced porcine plasma (test solution 3) is divided into 3 samples (A, B and C) of 40 ml plasma, 1 ml of water glass (Borup Kemi, Denmark) is added. pH was adjusted in all solutions to 6.0 with 1 M HCl. Following incubation for 60 minutes with stirring at ambient temperature the samples are centrifuged for 10 min at 1430 G, the supernatants are collected (test solutions 4-6).

The precipitate remaining in the centrifuge tubes are washed by re-suspending in 30 ml water and then centrifuged again.

For the precipitate from solution A, the proteins are released by adding up to 40 ml with 0.1 M NaCl, while mixing the pH is raised slowly to 10.5 (with 1 M NaOH), at pH 8.0, 8.5, 9.0, 9.5, 10.0 and 10.5 a 1 ml sample was taken out respectively. The samples were centrifuged for 10 min at 1430 G and the supernatant (test solution 7-12) was separated from the precipitate.

For the precipitate from solution B, the proteins are released by adding up to 40 ml with water, while mixing the pH is raised slowly to 10.5 (with 1 M NaOH), at pH 8.0, 8.5, 9.0, 9.5, 10.0 and 10.5 a 1 ml sample was taken out respectively. The samples were centrifuged for 10 min at 1430 G and the supernatant (test solution 13-18) was separated from the precipitate.

For the precipitate from solution C, the proteins are released by adding up to 40 ml with water, while mixing the pH is decreased slowly to 2.0, at pH 4.0, 3.5, 3.0, 2.5 and 2.0 a 1 ml sample was taken out respectively. The samples were centrifuged for 10 min at 1430 G and the supernatant (test solution 19-23) was separated from the precipitate.

Figure 9A:
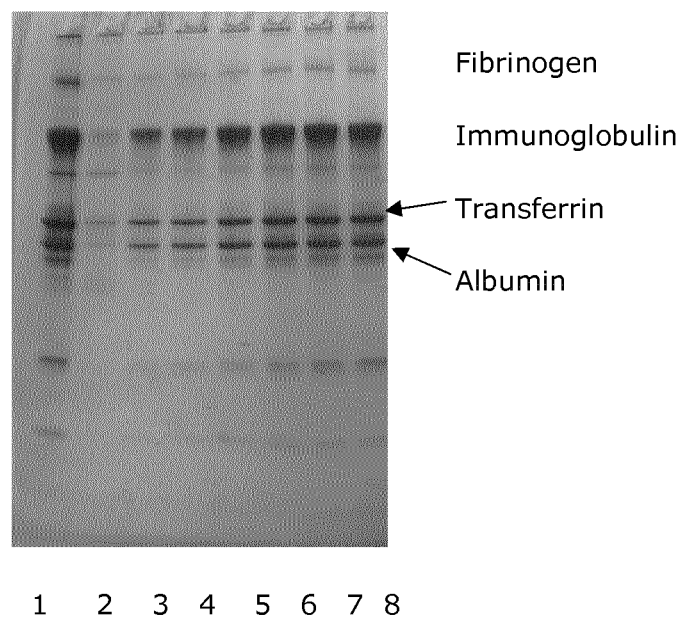
FIG. 9A is a Coomassie Blue stained SDS-PAGE gel illustrating the separation of proteins of test solutions 3, 4, and 7-12 described in Example 12.
Figure 9B:
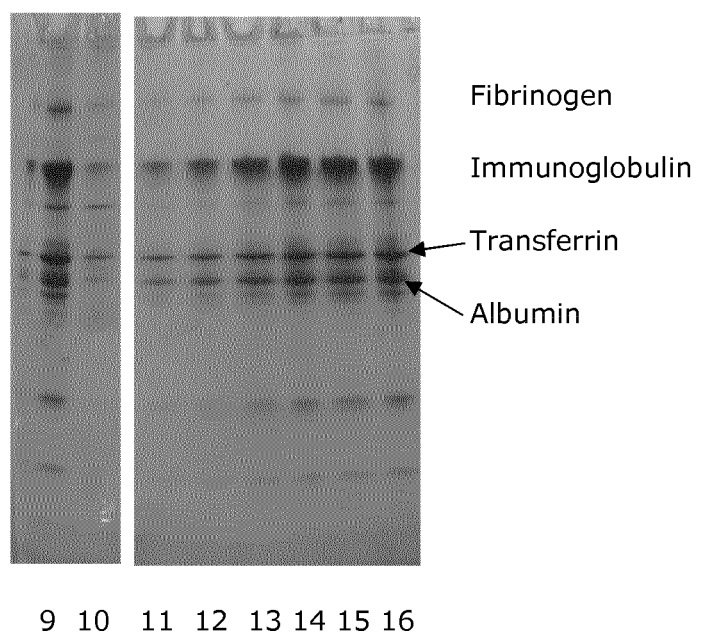
FIG. 9B is a Coomassie Blue stained SDS-PAGE gel illustrating the separation of proteins of test solutions 3, 5, and 13-18 described in Example 12.
Figure 9C:
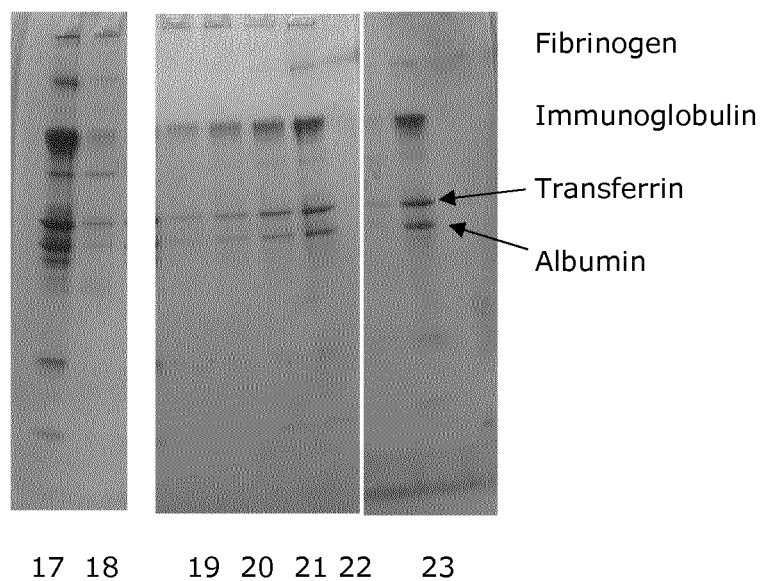
FIG. 9C is a Coomassie Blue stained SDS-PAGE gel illustrating the separation of proteins of test solutions 3, 6 and 19-23 described in Example 12.

SDS-PAGE is performed on test solution 3-23 as illustrated in FIGS. 9a, 9b and 9c.

FIG. 9a:
Lane 1: Albumin reduced porcine plasma, test solution 3
Lane 2: Supernatant, 500 µl water glass, test solution 4
Lane 3: Supernatant 0.1 M NaCl pH 8, test solution 7
Lane 4: Supernatant 0.1 M NaCl pH 8.5, test solution 8
Lane 5: Supernatant 0.1 M NaCl pH 9, test solution 9
Lane 6: Supernatant 0.1 M NaCl pH 9.5, test solution 10
Lane 7: Supernatant 0.1 M NaCl pH 10, test solution 11
Lane 8: Supernatant 0.1 M NaCl pH 10.5, test solution 12
FIG. 9b:
Lane 9: Albumin reduced porcine plasma, test solution 3
Lane 10: Supernatant, 500 µl water glass, test solution 5
Lane 11: Supernatant water pH 8, test solution 13
Lane 12: Supernatant water pH 8.5, test solution 14
Lane 13: Supernatant water pH 9, test solution 15
Lane 14: Supernatant water pH 9.5, test solution 16
Lane 15: Supernatant water pH 10, test solution 17
Lane 16: Supernatant water pH 10.5, test solution 18
FIG. 9c:
Lane 17: Albumin reduced porcine plasma, test solution 3
Lane 18: Supernatant, 500 µl water glass, test solution 6
Lane 19: Supernatant water pH 4, test solution 19
Lane 20: Supernatant water pH 3.5, test solution 20

Lane 21: Supernatant water pH 3, test solution 21
Lane 22: Supernatant water pH 2.5, test solution 22
Lane 23: Supernatant water pH 2, test solution 23

The SDS PAGE analysis of FIGS. 9a, 9b and 9c, illustrates that the sodium metasilicate solution is capable of precipitating practically all the protein present in the albumin reduced porcine plasma (lane 2, 10 and 18), there are practically no protein bands in the supernatant samples. When pH is increased the proteins are released from the precipitate, as can be seen the higher pH the more protein bands appear in the supernatant. At pH 8, 8.5 and 9 only a fraction of the protein is released (lane 7, 8 and 9 and lane 13, 14 and 15). At 9.5, 10 and 10.5 practically all the proteins are released except fibrinogen. More than 90% of the silicate remains precipitated at all of these pH-values.

At low pH-values (FIG. 9c, pH 2-4) some proteins are released selectively from the silicate precipitate. The lower pH the more protein and at pH 2-2.5 a major part of the immunoglobulin is released. Fibrinogen and several other protein bands are not released at all from the silicate precipitate. At the low pH-values the silicate remains completely precipitated and the immunoglobulin is highly enriched compared to the starting material and contains practically no silicate. Also, the initial red/yellow colour, the minerals and lipids and the smell characteristic of porcine plasma was eliminated from the immunoglobulin solution released from the precipitate.

The invention claimed is:

1. A method for isolating one or more proteins from an aqueous protein solution comprising one or more proteins and impurities, the method comprising;
   a. providing an aqueous solution containing one or more proteins and impurities,
   b. adding a water-soluble silicate to the aqueous solution of step a) such that the total concentration of silicon in the form of free or complexed silicates in the aqueous solution is in the range of 1-1000 mM,
   c. adjusting the pH of the resulting aqueous solution to a pH in the range of pH 5-7,
   d. allowing the silicate to form an insoluble precipitate of a silicate-protein complex,
   e. separating the silicate-protein complex from the aqueous solution as a wet precipitate;
   f. optionally washing the silicate-protein complex to further remove said impurities from the silicate-protein complex,
   g. separating the one or more proteins from the silicate, wherein the separation in step g) is done by;
      raising the pH to more than 7, or
      raising pH to a pH of more than 10 to solubilize the silicate-protein complex allowing the silicate to be separated from the protein by a method selected from the group consisting of membrane filtration, selective silicate precipitation with metal-ions, selective precipitation of the protein, adsorption chromatography, selective precipitation with metal-ions, chromatography, ultrafiltration, and combinations thereof, or
      lowering pH to below pH 5,
   thereby obtaining the isolated protein product.

2. The method according to claim 1 wherein said washing step f) is mandatory.

3. The method according to claim 1 wherein said separating step g) is mandatory.

4. The method according to claim 1 further comprising a step of clarification to remove insoluble and/or colloid particles prior to step b).

5. The method according to claim 1, wherein the separation of the one or more proteins from the silicate is done by adjusting the pH of the wet precipitate to a pH in the range pH 7 to pH 11, such that the one or more proteins are released into solution from the precipitate while at least 50 of the silicate in the protein-silicate complex remains in the form of an insoluble precipitate.

6. The method according to claim 1, wherein the separation of the one or more proteins from the silicate is done by adjusting pH to below pH 5.0 such that the one or more proteins are released into the solution from the precipitate while at least 50% of the silicate in the protein-silicate complex remains in the form of an insoluble precipitate.

7. The method according to claim 1, wherein the separation of the one or more proteins from the silicate is done by adjusting pH of the wet precipitate to a pH in the range of pH 9 to pH 13, to solubilize the silicate-protein complex followed by allowing the silicate to be separated from the protein by a method selected from the group consisting of membrane filtration such as ultrafiltration using a membrane allowing the selective passage of silicate ions, selective silicate precipitation with metal-ions, selective precipitation of the protein, and adsorption chromatography such as ion exchange.

8. The method according to claim 1, wherein the one or more proteins are a vegetable protein, a mammalian protein, a protein originating from fish, a protein originating from algae, a protein originating om fungi or a protein originating from microorganisms.

9. The method according to claim 1, wherein the one or more proteins are potato proteins, mammalian plasma proteins, single cell proteins, yeast proteins or egg proteins.

10. The method according to claim 1, wherein said one or more proteins are one or more first proteins, and said impurities comprise one or more second proteins, such that the method provides the separated one or more first proteins and said one or more second proteins in two different fractions.

11. A method for purifying a protein in an aqueous solution comprising impurities, the method comprising;
   a. providing an aqueous solution containing the protein and the impurities at 2-12,
   b. adding a soluble silicate to the aqueous solution of step a) such that the concentration of silicon (in the form of silicate) in the aqueous solution is in the range of 1-500 mM,
   c. adjusting the pH of the resulting aqueous solution to pH 5-7,
   d. allowing the silicate to form an insoluble silicate-protein complex,
   e. separating the silicate-protein complex from the aqueous solution, and
   f. separating the protein from the silicate,
   wherein the separation in step f) is done by;
      raising the pH to more than 7, or
      raising pH to a pH of more than 10 to solubilize the silicate-protein complex allowing the silicate to be separated from the protein by a method selected from the group consisting of membrane filtration, selective silicate precipitation with metal-ions, selective precipitation of the protein, adsorption chromatography, selective precipitation with metal-ions, chromatography, ultrafiltration, and combinations thereof, or
      lowering pH to below pH 5,
   thereby obtaining the purified protein.

12. The method according to claim 11, further comprising a washing step after step e).

13. The method according to claim 11, wherein the protein is a vegetable protein, a mammalian protein, a protein originating from a fish, a protein originating from algae, or a protein originating form seaweed.

14. The method according to claim 11, wherein the protein is from a potato.

15. The method according to claim 11, wherein the protein is mammalian.

16. The method according to claim 15, wherein the protein is from a mammalian cell culture or a culture of genetically modified microorganisms.

17. The method according to claim 1, wherein said wet precipitate is a wet cake or an aqueous suspension of the precipitate.

* * * * *

UNITED STATES PATENT AND TRADEMARK OFFICE
CERTIFICATE OF CORRECTION

PATENT NO. : 11,623,942 B2
APPLICATION NO. : 16/491970
DATED : April 11, 2023
INVENTOR(S) : Allan Otto Fog Lihme et al.

It is certified that error appears in the above-identified patent and that said Letters Patent is hereby corrected as shown below:

In the Claims

Column 22, Claim 5, Line 3, after "range" insert -- of --.

Column 22, Claim 5, Line 5, change "50" to -- 50% --.

Column 22, Claim 7, Line 15, after "done by" insert -- first --.

Column 22, Claim 7, Line 16, after "adjusting" insert -- the --.

Column 22, Claim 8, Line 28, change "om" to -- from --.

Column 22, Claim 11, Line 42, after "at" insert -- pH --.

Column 23, Claim 13, Line 6, change "form" to -- from --.

Signed and Sealed this
First Day of August, 2023

Katherine Kelly Vidal
Director of the United States Patent and Trademark Office